United States Patent [19]

Nobuhara et al.

[11] Patent Number: 4,465,622
[45] Date of Patent: Aug. 14, 1984

[54] METHOD FOR PURIFYING INTERFERON

[75] Inventors: Masahiro Nobuhara; Kiyoshi Yamaguchi, both of Saitama; Ei Mochida, Tokyo, all of Japan

[73] Assignee: Mochida Pharmaceutical Co., Ltd., Tokyo, Japan

[21] Appl. No.: 385,872

[22] Filed: Jun. 7, 1982

[30] Foreign Application Priority Data

Jul. 29, 1981 [JP] Japan ............................. 56-118865

[51] Int. Cl.$^3$ ..................... C07C 103/52; A61K 45/02
[52] U.S. Cl. .................................... 260/112 R; 424/85
[58] Field of Search ...................... 260/112 R; 424/85

[56] References Cited

U.S. PATENT DOCUMENTS 4,168,261  9/1979  Edy ........................................ 424/85
4,172,071  10/1979  De Maeyer et al. ................ 424/85

OTHER PUBLICATIONS

Chemical Abstracts, vol. 90, p. 274, Abst. No. 156689a, 1979.
Rubinstein et al., Arch. Biochem. Biophys., vol. 210, pp. 307–318, 1981.
Whitman et al., J. Interferon Research, vol. 1, pp. 305–312, 1981.
Heine et al., J. Gen. Virol., vol. 54, pp. 47–56, 1981.
Yip et al., Proc. Natl. Acad. Sci., vol. 78, pp. 1601–1605, 1981.
Yonehara et al., J. Biol. Chem., vol. 256, pp. 3770–3775, 1981.
Knight, Jr. et al., J. Biol, Chem., vol. 256, pp. 3609–3611, 1981.

*Primary Examiner*—Blondel Hazel
*Attorney, Agent, or Firm*—Parkhurst & Oliff

[57]  ABSTRACT

A method for purifying interferon having anti-cancer effects or anti-viral effects, wherein highly purified interferon can be easily obtained by a single operation in a recovery of about 100%. In this method, interferon is obtained by specifically adsorbing interferon onto a carrier containing acrylonitrile polymer and eluting the adsorbed interferon with an appropriate buffer.

19 Claims, No Drawings

METHOD FOR PURIFYING INTERFERON

This invention relates to a method for purifying interferon. Interferon is a protein which is produced upon infection by viruses, or by an immuno-reaction such as an antigen-antibody reaction. Interferon has an antiviral effect.

There have been known several processes to produce interferon. Leukocytes or lymphoblastoid cells can be stimulated to produce interferon with appropriate viruses or lectins.

Fibroblast cells can also be stimulated to produce interferon with viruses or a synthetic nucleic acid.

Furthermore, recent developments in recombinant DNA technology make it possible to produce interferon, not by the culture of mammalian cells, but by the culture of microorganisms, such as Saccharomyces cerevisiae, Escherichia coli and Bacillus subtilis, which are transformed with a plasmid that carries an interferon gene.

Interferon is classified into three categories according to its origins. Leukocytes and lymphoblastoid cells stimulated with viruses produce interferon-alpha, those cells stimulated with lectins produce interferon-gamma, and fibroblast cells stimulated with a synthetic nucleic acid produce interferon-beta.

In recent years, clinical trials on these three types, especially alpha and beta types, of interferon as an antitumor or anti-viral agent have been conducted. But at present, the purity of interferon preparations for clinical use is around 0.01–1.0% in both interferon-alpha and -beta. Side effects, e.g. pyrexia, allergy, etc. presumably due to contaminants, have been reported, so that the development of highly purified interferon preparations has been desired.

A number of investigations into purifying interferon have been carried out, for instance, based on affinity chromatography; CPG (Edy, V. G. et al., J. Gen. Virol., Vol. 33, 517–521, 1976), zinc chelates (Edy, V. G. et al., J. Biol. Chem., Vol. 252, 5934–5935, 1977), concanavalin A (Davey, M. W. et al., Biochem., Vol. 15, 704–713, 1976; Carter, W. A. et al., Pharmac. Ther., Vol. 8, 359–377, 1980), anti-interferon antibody (Berg, K. et al., J. Immunol., Vol. 114, 640–644, 1975), or based on a method with KSCN (Cantell, K. et al., Pharmac. Ther. C., Vol. 1, 369, 1977). However, none of these methods adequately meet both the recovery rate and the purity desired, and each falls into the following dilemma: preparing a highly purified interferon would result in reduction of the recovery rate, while a high recovery rate would, in turn, result in low purity.

SUMMARY OF THE INVENTION

Under such circumstances, the present inventors have been intensively studying for many years, and finally discovered that an adsorbent which contains acrylonitrile high polymer specifically adsorbs interferon. Highly purified interferon can be easily obtained with an almost 100% recovery rate by a single step elution of interferon with an appropriate buffer.

The main object of the present invention is, therefore, to provide a method for purifying interferon, which is characterized by contacting a solution containing interferon with one or more adsorbents containing acrylonitrile high polymer to adsorb the interferon onto the adsorbent, and thereafter eluting it.

Another object of the present invention is to provide a method for purifying interferon by which interferon of high purity can be obtained in a recovery yield of almost 100%.

A further object of the present invention is to provide a method for purifying interferon, in which an aqueous solution of ordinary organic substances is used as an eluant.

A still further object of the present invention is to provide a method for purifying interferon, in which protein, sugar or amino acid is added to the eluate for the stabilization of interferon in it.

The present invention is not only applicable to the purification of interferon produced by mammalian cells but also applicable to the purification of interferon produced by any other procedure, for instance, by the recombinant DNA technique, etc.

DETAILED DESCRIPTION OF THE INVENTION

The general procedure for the purification of interferon according to this invention is as follows: (a) A solution containing interferon is adjusted to pH 4.0–8.5, preferably 5.0–8.0, (b) the solution is contacted with one or more adsorbents containing acrylonitrile high polymer by a column method or a batch method to adsorb interferon onto the adsorbent, and (c) thereafter the interferon is recovered with an appropriate solution.

Suitable adsorbents which are used in this invention are preferably fiber materials which contain acrylonitrile high polymer, but the adsorbents are not limited to fiber materials. The fibers containing acrylonitrile are classified in Japan according to the regulations for indication of quality, i.e. those containing 50% by weight or more of acrylonitrile are called 'acryl', and those containing less than the above are called 'acrylic'; or in the United States, the term acryl is used for those containing 85% by weight or more of acrylonitrile and the term modacryl is used for those containing 35–85% (exclusive) by weight. In this invention, since any of the fibers given above can specifically adsorb and elute interferon, there is no need to distinguish them and therefore all of them are included in the adsorbent of this invention.

As such fibers, there may be mentioned, for instance, Cashimilon (trademark—95% or more acrylonitrile acryl fiber) (Asahi Chemical), Kanebo Acryl (trademark—85% or more acrylonitrile acryl fiber) (Kanebo), Kanekalon (trademark—60% acrylonitrile, 40% vinyl chloride modacryl fiber) (Kanebo), Vonnel (trademark—85% or more acrylonitrile, vinyl acetate, vinyl pyridine acryl fiber) (Mitsubishi Rayon), Exlan (trademark—85% or more acrylonitrile, acrylamide, alkyl pyridine acryl fiber) (Japan Exlan), Beslon (trademark—95% or more acrylonitrile acryl fiber) (Toho Beslon), Toraylon (trademark—95% or more acrylonitrile acryl fiber) (Toray), Pewlon (trademark—85% or more acrylonitrile acryl fiber) (Asahi Chemical), Silpalon (Mitsubishi Rayon), Promix (trademark—85% or more acrylonitrile, casein acryl fiber) (Toyo Spinning); Orlon (trademark—about 100% acrylonitrile acryl fiber), Acrilan (trademark—85% or more acrylonitrile, 2-vinyl pyridine, vinyl acetate acryl fiber), Creslan (trademark—acrylonitrile, acrylamide acryl fiber), Zefran (trademark—acrylonitrile, N-vinyl-2-pyrrolidone acryl fiber), Verel (trademark—60% acrylonitrile, 40% vinylidene chloride modacryl fiber), Dynel (trademark—40 or 60% acrylonitrile, 60 or 40% vinyl chloride modacryl fiber), Vinyon N (trademark—35-85% acrylonitrile modacryl fiber) in the United States; Courtelle (trademark—85% or more acrylonitrile acryl fiber), Teklan (trademark—50% acrylonitrile, 50% vinylidene chloride modacryl fiber), in the United Kingdom; Pan (trademark—85% or more acrylonitrile acryl fiber), Dralon (trademark—85% or more acrylonitrile acryl fiber) in West Germany; etc. Any forms other than fibers, such as sponges, powders, flakes, porous granules, films, linear molded products or secondary processed products thereof, may also be employed. In this connection, the acrylonitrile high polymer may also contain comonomer components such as methyl acrylate, methyl methacrylate, acrylic acid, methacrylic acid, vinyl acetate, vinyl chloride, vinylidene chloride, etc.

There is no particular restriction on the eluant for interferon so long as it can elute interferon from the adsorbent containing acrylonitrile high polymer, and good results are obtained with an aqueous solution of ordinary organic or inorganic substances such as sodium chloride, ammonium chloride, phosphates, acetates, amino acids, alcohols, alkylene glycols, polyalkylene glycols, dimethyl sulfoxide, etc.

Although the pH of the eluant in a range of pH 2-9 is generally preferable because of the stability of interferon, it is not necessary to insist on this pH range. For example, in the case that elution would be performed by using a pH 10 eluant, there would not be any problem as the pH of the eluate is brought back to an appropriate pH where the interferon is stable. Further, it is also possible to stabilize interferon in the eluate by adding about 0.005-1% of protein such as human serum albumin, gelatin, etc., about 1-10% of sugar such as sucrose, mannitol, glucose, etc., or about 0.01-1% of amino acid such as glycine, cystine, etc., to the eluate.

Comparison between examples of this invention and conventional processes is described below, but it should be noted that this invention is not limited to these examples. Crude solutions of interferon to be purified as shown in the examples were produced as follows:

A. Human fibroblast cells were cultured by using Eagle's Minimum Essential Medium (MEM) supplemented with 10% bovine fetal serum until they reach confluency, and interferon beta (IFN-beta) was obtained from the culture according to the process described by Mozes, L. W. et al. (Virology, Volk. 65, 100-111, 1975). The content of IFN-beta was 6500 International Units per milliliter (IU/ml).

B. From human leukocytes, interferon alpha (IFN-alpha) was obtained according to the process described by Strander, H. et al., (Ann. Med. Exp. Fenn., Vol. 44, 265-273, 1966). The content of IFN-alpha was 104,000 IU/ml.

C. From a human lymphoblastoid cell line (Namalwa), an interferon solution containing mainly IFN-alpha (10,200 IU/ml) was obtained according to the process described by Strander, H. et al., supra.

Example 1

One thousand milliliters ($6.5 \times 10^6$ IU) of IFN-beta obtained by method A described above was adjusted to pH 6.0 with 0.5 N acetic acid, and passed through a column packed with 5 g. of polyacrylonitrile fiber (tradename: Vonnel, Mitshubishi Rayon), to adsorb IFN-beta on the column. The column was washed with 500 ml of 0.1 M phosphate buffer (pH 7.4), and then the IFN-beta was eluted with 300 ml of 3 M $NH_4Cl$.

Example 2

One thousand milliliters ($6.5 \times 10^6$ IU) of IFN-beta obtained by method A was adjusted to pH 8.0 with 0.5 N aqueous ammonia and passed through a column packed with 4.6 g. of polyacrylonitrile fiber (tradename: Cashimilon, Asahi Chemical), to adsorb IFN-beta on the column. The column was washed with 200 ml of 1 M NaCl and then the IFN-beta was eluted with 100 ml of 0.5 M NaCl/50% ethylene glycol solution.

Example 3

Two thousand milliliters of IFN-beta obtained by method A was adjusted to pH 7.0 with 0.01 N hydrochloric acid and passed through a column packed with 6.5 g. of polyacrylonitrile fiber (tradename: Torelon, Toray), and then the column was washed with 450 ml 0.01 M phosphate buffer containing 1 M NaCl. Thereafter, IFN-beta was eluted from the column by 100 ml of 1 M NaCl/60% propyleneglycol solution.

Comparison of the results with those of conventional processes is shown in Table 1.

TABLE 1

|  |  | Recovery Yield (%) | Specific Activity (IU/mg) |
|---|---|---|---|
| Process of the Invention | Example 1 | 109 | $2.3 \times 10^7$ |
|  | Example 2 | 97 | $6.8 \times 10^7$ |
|  | Example 3 | 102 | $9.0 \times 10^7$ |
| Conventional Process | Concanavalin A* | 52 | $1.0 \times 10^6$ |
|  | Zn Chelate** | 57 | $1.3 \times 10^6$ |

*According to the process by Davey, M. W. et al., (Biochim., Vol. 15, 704-713, 1976).
**According to the process by Edy, V. G. et al., (J. Biol. Chem., Vol. 252, 5934-5935, 1977).

As shown in Table 1, it is evident that the method of purification according to this invention is superior as compared with conventional methods from both aspects of recovery yield and purity.

Example 4

A solution of interferon alpha (IFN-alpha) obtained by method B was adjusted to pH 5.5 with 0.1 N HCl, and to 50 ml ($5 \times 10^6$ IU) of this solution was added 1.5 g. of polyacrylonitrile beads and, after stirring for 60 minutes, the beads were recovered with the interferon adsorbed on them. After washing the beads with 30 ml of 0.01 M phosphate buffer (pH 7.0), interferon was eluted with 10 ml of 0.1 M phosphate buffer (pH 8.0)/0.3 M NaCl.

Example 5

Two thousand milliliters of the solution obtained by method C, which contains IFN-alpha as the main component, was adjusted to pH 4.0 with 0.1 N acetic acid and passed through a column packed with 5 g. of polyacrylonitrile fiber. The column was then washed with 400 ml of 0.01 M phosphate buffer (pH 6.5), and thereafter eluted with 150 ml of 0.05 M phosphate buffer (pH 7.5)/0.5 M NaCl/30% ethylene glycol solution.

TABLE 2

|  | Process of the Invention | | Conventional Process Process by Cantell, K. et al.* |
|---|---|---|---|
|  | Example 4 | Example 5 |  |
| Recovery Yield | 108% | 100% | 50% |
| Specific | $2 \times 10^7$ | $32 \times 10^7$ | $1.4 \times 10^7$ IU/mg |

TABLE 2-continued

| | Process of the Invention | | Conventional Process Process by Cantell, K. et al.* |
|---|---|---|---|
| | Example 4 | Example 5 | |
| Activity | IU/mg | IU/mg | |

*Cantell, K. et al. (Pharmac. Ther. C., Vol. 1, 369, 1977)

As in Table 1, superiority of this invention is evident.

As has been described above, the method of purification according to this invention is highly efficient. Thus, it enables one to recover interferon of high purity in a recovery rate of about 100% by a single simple operation. The method of purification according to this invention is generally applicable to purifying interferon. This method is very useful not only for purifying interferon produced by mammalian cells but also that produced by any other procedures other than the above, for instance, interferon obtained by the recombinant DNA technique, etc.

What is claimed is:

1. A method for purifying interferon comprising contacting a solution containing interferon with one or more interferon adsorbing effective adsorbents which contain a high polymer of acrylonitrile to adsorb the interferon onto said adsorbent, and thereafter eluting the interferon with an interferon eluting effective eluant to produce an eluate.

2. A method for purifying interferon as claimed in claim 1, wherein the adsorbent comprises fiber material containing a high polymer of acrylonitrile.

3. A method for purifying interferon as claimed in claim 1 or 2, wherein the fiber material containing a high polymer of acrylonitrile comprises Cashimilon (trademark), Kanebo Acryl (trademark), Kanekalon (trademark), Vonnel (trademark), Exlan (trademark), Beslon (trademark), Toraylon (trademark), Pewlon (trademark), Promix (trademark), Orlon (trademark), Acrilan (trademark), Creslan (trademark), Zefran (trademark), Verel (trademark), Dynel (trademark), Vinyon N (trademark), Courtelle (trademark), Teklan (trademark), Pan (trademark) or Dralon (trademark).

4. A method for purifying interferon as claimed in claim 1 or 2 or 5 wherein the high polymer of acrylonitrile contains as a comonomer component methyl acrylate, methyl methacrylate, acrylic acid, methacrylic acid, vinyl acetate, vinyl chloride, or vinylidene chloride.

5. A method for purifying interferon as claimed in claim 1, wherein the pH of the eluant is adjusted to the range from pH 2 to 9.

6. A method for purifying interferon as claimed in claim 5, wherein the pH of the eluant is adjusted to the range from pH 5.0 to 8.0.

7. A method for purifying interferon as claimed in claim 1, wherein the pH of the eluate is immediately brought back to approximately neutral if the pH of the eluant is outside of the range from pH 2 to 9.

8. A method for purifying interferon as claimed in claim 1, wherein the eluant for interferon is an aqueous solution containing dimethyl sulfoxide.

9. A method for purifying interferon as claimed in claim 1, wherein the adsorbent comprises beads containing a high polymer of acrylonitrile.

10. A method for purifying interferon as claimed in claim 1, wherein the eluant for interferon is an aqueous solution containing sodium chloride, amonium chloride or phosphates.

11. A method for purifying interferon as claimed in claim 1, wherein the eluant for interferon is an aqueous solution containing ethylene glycol or propylene glycol.

12. A method for purifying interferon as claimed in claim 1 or 2, wherein the high polymer of acrylonitrile is an acryl fiber containing 85% by weight or more of acrylonitrile.

13. A method for purifying interferon as claimed in claim 1 or 2, wherein the high polymer of acrylonitrile is a modacryl fiber containing 35-85% by weight of acrylonitrile.

14. A method for purifying interferon as claimed in claim 1, 8, 10 or 11, wherein human serum albumin or gelatin is added to the eluate for the stabilization of interferon in the eluate.

15. A method for purifying interferon as claimed in claim 14, wherein said human serum albumin or gelatin is added in an amount of 0.005-1%.

16. A method for purifying interferon as claimed in claim 1, 8, 10 or 11, wherein sucrose, mannitol or glucose is added to the eluate for the stabilization of interferon in the eluate.

17. A method for purifying interferon as claimed in claim 16, wherein said sucrose, mannitol or glucose is added in an amount of 1-10%.

18. A method for purifying interferon as claimed in claim 1, 8, 10 or 11, wherein glycine or cystine is added to the eluate for the stabilization of interferon in the eluate.

19. A method for purifying interferon as claimed in claim 18, wherein said glycine or cystine is added in an amount of approximately 0.01-1%.

* * * * *